United States Patent [19]

Bundesen et al.

[11] Patent Number: 4,758,524

[45] Date of Patent: Jul. 19, 1988

[54] MONOCLONAL ANTIBODIES WITH SPECIFICITY FOR CROSSLINKED FIBRIN DERIVATIVES AND ASSAY FOR SAID DERIVATIVES

[75] Inventors: Peter G. Bundesen, Ekibin; Dennis B. Rylatt, Rosalie, both of Australia

[73] Assignee: Fielder Gillespie David Limited, Sydney, Australia

[21] Appl. No.: 590,054

[22] Filed: Mar. 15, 1984

[30] Foreign Application Priority Data

Mar. 17, 1983 [AU] Australia .................... PF8494

[51] Int. Cl.$^4$ .................... G01N 33/53; C12N 15/00
[52] U.S. Cl. .................... 436/548; 435/172.2; 424/85; 935/110
[58] Field of Search .................... 435/172.2; 436/548, 436/68; 935/110

[56] References Cited

U.S. PATENT DOCUMENTS 4,196,265 4/1980 Koprowski .................... 435/172.2

OTHER PUBLICATIONS

Chemical Abstracts, vol. 99, Abstract No. 863006, 1983.
Chemical Abstracts, vol. 99, Abstract No. 86301c, 1983.
Chemical Abstracts, vol. 99, Abstract No. 209051f, 1983.
Chemical Abstracts, vol. 99, Abstract No. 118615b, 1983.
C. S. Cierniewski, A. Janiak, P. Nowak and W. Augustyniak, Thromb. Haemostas. 48(1) 33–37; (1982).
D. B. Rylatt, et al., "Thrombosis Research", vol. 31, No. 6, pp. 767–778, Sep. 15, 1983.
J. H. Sobel et al., "Biochemistry", Monoclonal Antibody to the Region of Fibronectin Involved in Cross-Linking to Human Fibrin, pp. 4175–4183, Aug. 30, 1983.
P. H. Ehrlich et al., "Biochemistry", Monoclonal Antibodies to—Chain Regions of Human Fibrinogen That Participate in Polymer Formation, pp. 4184–4192, Aug. 30, 1983.
J. Soria et al., Immuno Chemical Differentiation of Fibrinogen, Fragment D or E, and Cross–Linked Fibrin Degradation Products Using Monoclonal Antibodies, "Fibrinogen-Structure, Functional Aspects, Metabolism", vol. 2, 1983, pp. 228–233.

*Primary Examiner*—Blondel Hazel
*Attorney, Agent, or Firm*—Cushman, Darby & Cushman

[57] ABSTRACT

The invention relates to a method of a preparation of monoclonal antibody derived from a crosslinked fibrin derivative including the steps of:

(i) obtaining a crosslinked fibrin derivative or extract containing same; and
(ii) forming an antibody to said derivative or extract by cloning antibody producing cells from an animal having been administered thereto said derivative or extract.

A screening assay for use in the abovementioned method which includes the steps of:
(A) coating a surface with an antigen selected from a
 (i) crosslinked fibrin derivative;
 (ii) extract containing said derivative; or
 (iii) fibrinogen degradation product.
(B) contacting said antigen with a monoclonal antibody derived from crosslinked fibrin derivative; and
(C) subjecting the complex formed in step (A) to a signal amplification step and an assay procedure for detection of the presence of a crosslinked fibrin derivative in an animal body fluid including the steps of:
 (i) contacting a monoclonal antibody prepared from a crosslinked fibrin derivative with a fluid sample suspected of containing an antigen derived from a crosslinked fibrin derivative or comprising a crosslinked fibrin derivative per se; and
 (ii) subjecting the complex formed in step (i) to a signal amplification step are also provided.

15 Claims, 4 Drawing Sheets

MONOCLONAL ANTIBODIES WITH SPECIFICITY FOR CROSSLINKED FIBRIN DERIVATIVES AND ASSAY FOR SAID DERIVATIVES

BACKGROUND OF THE INVENTION

1. Field of the Invention

This invention relates to monoclonal antibodies derived from crosslinked fibrin derivatives and assays for said cross linked derivatives which may be used as a diagnostic test for fibrin breakdown products in fibrinolysis in general and pre-thrombotic and thrombotic states including Disseminated Intravascular Coagulation (DIC).

2. Description of the Related Art

Fibrinogen is a large protein molecule that normally circulates in the blood plasm in the dissolved state. Under attack from the enzyme thrombin, the fibrinogen molecules link up, spontaneously aligning themselves into a long thread like polymer or network called fibrin which is the primary ingredient of blood clots.

It has been discovered that upon digestion with an enzyme called plasmin (which functions in the blood to destroy the fibrin network and restore the fluidity of the plasma), fibrinogen breaks down into fragments designated by A-E. Fragments D and E made up the bulk of the recovered mass and there was about twice as much D as there was of E. Fibrogen also has been discovered to have a trinodular shape wherein E is a central component and D is a terminal component.

Plasmin digests of fibrin and fibrinogen can be differentiated from each other using polyacrylamide gel electrophoresis (PAGE). Crosslinking of fibrin with an enzyme called Factor XIIIa forms dimers of fragment D called D dimer. Factor XIIIa is an enzyme which introduces covalent bonds between adjacent monomers in fibrin and thus may stabilize the fibrin structure. For a more detailed explanation of the nature of the crosslinking between fibrin monomers, refer to Budzynski et al, Blood, Vol 54, No. 4 (October)1979. Factor XIIIa is activated by the thrombin-catalyzed removal of a peptide from a precursor in the plasma and in blood platelets. D dimer is a molecule of about 189,000 daltons which consists essentially of two fragment D moieties derived from different fibrin molecules covalently bound by cross link bonds between the gamma chain remnants of fibrinogen. Fibrinogen itself comprises 6 chains including two copies of an alpha, beta and gamma chain.

Another complex (DD)E is formed by plasmin degradation of cross linked human fibrin and comprises a combination of two D fragments and fragment E.

Other cross linked derivatives may be prepared as described in an article from Seminars in Thrombosis and Hemostasis Vol 8, No. 1 (1982) entitled "Detection and Relevance of Crosslinked Fibrin Derivatives in Blood" by Graeff and Halfer. These include high molecular weight cross linked derivatives and may be referred to in the above reference as derivatives DY, YY, XD, XY, DXD and YXD.

Normal hemostasis or coagulation of the blood involves maintaining intravascular constituents in a liquid phase or suspension while concomitantly permitting local deposition of solid phase blood components in areas of vessel damage. In a healthy individual, it has been assumed, but never experimentally demonstrated, that a balance exists between a low-grade intravascular deposition of fibrin and its removal by fibrinolysis or cellular phagocytosis.

Early clinical observations revealed that some severly ill patients developed signs of hemorrhage and massive bruising and had prolonged clotting times and thrombocytopenia. After death, in some cases, fibrin thrombi were demonstrated in the microvasculature. The diffuse nature of these thrombi gave rise to the term "disseminated intravascular coagulation" (DIC). Subsequently, coagulation factors were shown to be reduced. These findings give rise to the concept of "consumptive coagulapathy", a term sometimes used as a synonym for DIC.

The currently accepted sequence of events in DIC involves activation of the coagulation system resulting in platelet consumption, thrombin generation, fibrin deposition, and secondary fibrinolysis. The net biologic effect of this process reflects a balance between fibrin deposition and fibrin clearance. The resulting clinical manifestations may be hemorrhage, when depletion of coagulation factors predominates, or ischemic tissue damage due to the effects of vascular occlusion.

DIC has been reported as a secondary phenomenon in a wide variety of disorders, particularly those accompanied by a combination of shock, acidosis, and hypoxemia. The well-recognized clinical associations are sepsis, major trauma, malignancy, and obstetric disorders. In these clinical settings activation of the coagulation sequence results in consumption of coagulation protein and platelets, leading to fibrin deposition in the microcirculation. The precise factors that initiate the DIC are unknown, but many potential mechanisms have been demonstrated in animal experiments.

Ideally a definitive diagnosis of DIC should require the direct demonstration of diffuse fibrin deposition. The practical difficulty of obtaining multiple direct biopsy evidence to differentiate between localized and generalized fibrin formation has led to the development of indirect tests that are substituted as diagnostic end points. However these tests are not specific for the syndrome of intravascular fibrin deposition. There specificity is further reduced by the action of other enzymes that although are not able to convert fibrinogen to fibrin can cause similar alterations to thrombin on the other coagulation factors involved in thrombosis. All of the direct tests are based on the principle that thrombin is the only enzyme (snake venoms excluded) capable of converting fibrinogen to fibrin in man.

Also apart from the paracoagulation tests that detect the presence of circulating soluble fibrin monomer complexes, none of the more specific thrombin specific tests is readily available or useful for immediate clinical application in the diagnosis of clinical DIC. These tests include the FPA (fibrinopeptide A) test where FPA is measured by a specific RIA procedure, fibrin monomer assays, fibrinogen gel exclusion chromatography and tests for FPB (fibrinopeptide B) or thrombin increasable FPB.

Tests with biochemical nonspecificity for thrombin action include the prothombin time (PT) thromboplastin time (A PTT) and thrombin clotting time (TCT) tests. Although frequently useful in practice it must be recognized that information obtained from these tests is nonspecific in nature, acting as a measure of clotting factor depletion regardless of etiology.

Coagulation factor assays have also been found to be relatively non specific and these include assays for co-factors V and VIII as well as tests for fibrinogen levels.

Tests for fibrin-fibrinogen degradation products so far have not proved to be specific for the action of plasmin on fibrin and may yield positive results where there has been fibrinogenolysis without prior thrombin action on the fibrinogen molecule. These tests include tests for fragments D and E.

Tests for thrombin-mediated platelet interaction or release have been found to be nonspecific in nature. These include platelet count, platelet survival and tests of platelet release.

The use of radio labelled fibrinogen in relation to identifying clotting factors have also been attempted but found to be time consuming and difficult to perform.

Thus, in summary of the prior art, the efficacy of a diagnostic test lies in the ability to indicate the presence or absence of disease. There are well recognized essential design principles for studies determining the efficacy of a diagnostic test which enables the four indices of sensitivity, specificity, positive predictive value, and negative predictive value to be determined. The first requirement is the adoption of a suitable standard for diagnosis. Ideally, this standard should be slightly more than a clinical definition and should be as specific as possible for the disease entity. An inherent difficulty in relation to DIC is the absence of a comprehensive definition of this disorder. The clinical picture is very non-specific. Many of the routinely available laboratory tests also lack diagnostic specificity. A low platelet count suppots the likelihood of DIC but may occur as an isolated finding secondary to infection. Similar limitations apply to many of the coagulation assays. Hypofibrinogenemia does not distinguish between primary fibrinolysis, due either to the action of plasmin or elastases, and secondary fibrinolysis following the thrombin-medicated conversion of fibrinogen to fibrin. Alternatively, sensitive tests of thrombin action are available, but there are obvious drawbacks with their clinical use. An example is the FPA assay, which, although specific for thrombin action, is exquisitely sensitive and may detect localized intravascular coagulation yielding a positive result in uncomplicated venous thrombosis. The clinical significance of an elevated FPA level, even with a positive paracoagulation test, is then at issue, particularly if the platelet count, global clotting tests, and fibrinogen level are normal.

For these reasons, sensitivity, specificity, and predictive values cannot be determined in a standard fashion. The clinical presentation of the disorder is complex and unpredictable. The application of the available tests for diagnosis are therefore best considered in relation to the different clinical syndromes of intravascular coagulation.

It has also been proposed to assay for D dimer as a diagnostic test for DIC. However, this has necessitated the use of PAGE as described previously and this technique is far too cumbersome for routine clinical use. Antibodies have been raised to fibrin derived D-D-E fragments but in their current form these cross react with fibrinogen fragment D derivatives and as yet are unsuitable for clinical use.

A useful summary of DIC and conventional diagnostic tests will be found in *Seminars in Thrombosis and Hemostasis* Vol 8, No. 3(1982) and an article entitled *DIC; The Application and Utility of Diagnostic Tests* by Ockelford and Carter.

In the abovementioned *Budzynski* reference describes the study of polyclonal anti-D dimer antibodies using two different antisera. In this test antibodies were raised against specific markers on the D dimer molecule. In the test antisera were obtained in chickens and rabbits against a mixture (1:1) of $D_2E$ complex and D dimer and against D dimer exposed to 3M area at pH 5.5. It was however stated in this reference that it was hoped by the authors that the results of this test could be applied to clinical situations, such as the distinction between disseminated intravascular coagulation and primary fibrinogenolysis, since circulating fragment D dimer should be present in the former conditions but not in the latter. However, such application would require a much higher difference in reactivity between fragments D dimer and D, since this and other relevant clinical states have high concentrations of circulating fibrinogen derivatives in addition to the crosslinked fibrin fragments. It was also considered that although it was shown that the assays could be performed even in the presence of enormous concentrations of fibrinogen, further development of the antibody specificity was needed before it can be reliably applied to the relevant clinical situations.

The abovementioned Graeff and Hafter article also points out that crosslinked fibrin derivatives in blood such as D dimer may be considered as a marker for DIC. However, there is nothing in this article to demonstrate that a reliable diagnostic test for DIC could be devised based on crosslinked fibrin derivatives.

It is therefore an object of the present invention to provide an assay procedure for crosslinked fibrin derivatives which may be used on a clinical basis.

SUMMARY OF INVENTION

The invention provides a method of preparation for a monoclonal antibody derived from a crosslinked fibrin derivative including the steps of:
(i) obtaining a crosslinked fibrin derivative or extract containing same, and
(ii) forming an antibody to said derivative or said extract by cloning antibody producing cells from an animal having been administered thereto said derivative or said extract.

In step (i) a suitable antigenic extract could be obtained from plasmic degradation of fibrin clots or by simultaneous action of thrombin, Factor XIIIa and plasmin on fibrinogen with transient clot formation and subsequent clot lysis. In the latter method and the fibrinogen is converted to fibrin by the action of thrombin and Factor XIIIa and subsequently digested with plasmin. It will of course be appreciated that the fibrin derivative or extract containing same may be obtained from a human or other suitable animal source.

DETAILED DESCRIPTION OF THE INVENTION AND EXAMPLES BRIEF DESCRIPTION OF THE DRAWINGS

FIG. 1 describes a specific assay for D dimer. D dimer specific monoclonal DD-3B6/22 10 μg/ml was coated in the wells of a micro plate and reacted first with either D dimer (□—□), fibrinogen degradation products (Δ—Δ), fibrinogen (∎—∎), fibrin degradation products (●—●), fragment D (o — o) and then tagged with peroxidase conjugated DD-4D2/182.

FIG. 2 describes panaspecific MAb DD-4D2/182 10 μg/ml was coated on to the wells of a micro plate and reacted first with either D dimer (□—□), fibrin degradation products (●—●), fibrinogen (∎—∎), fibrinogen degradation products (Δ—Δ) and fragment D (o—o) and then tagged with peroxidase conjugated DD-1C3/108.

Figure 1:
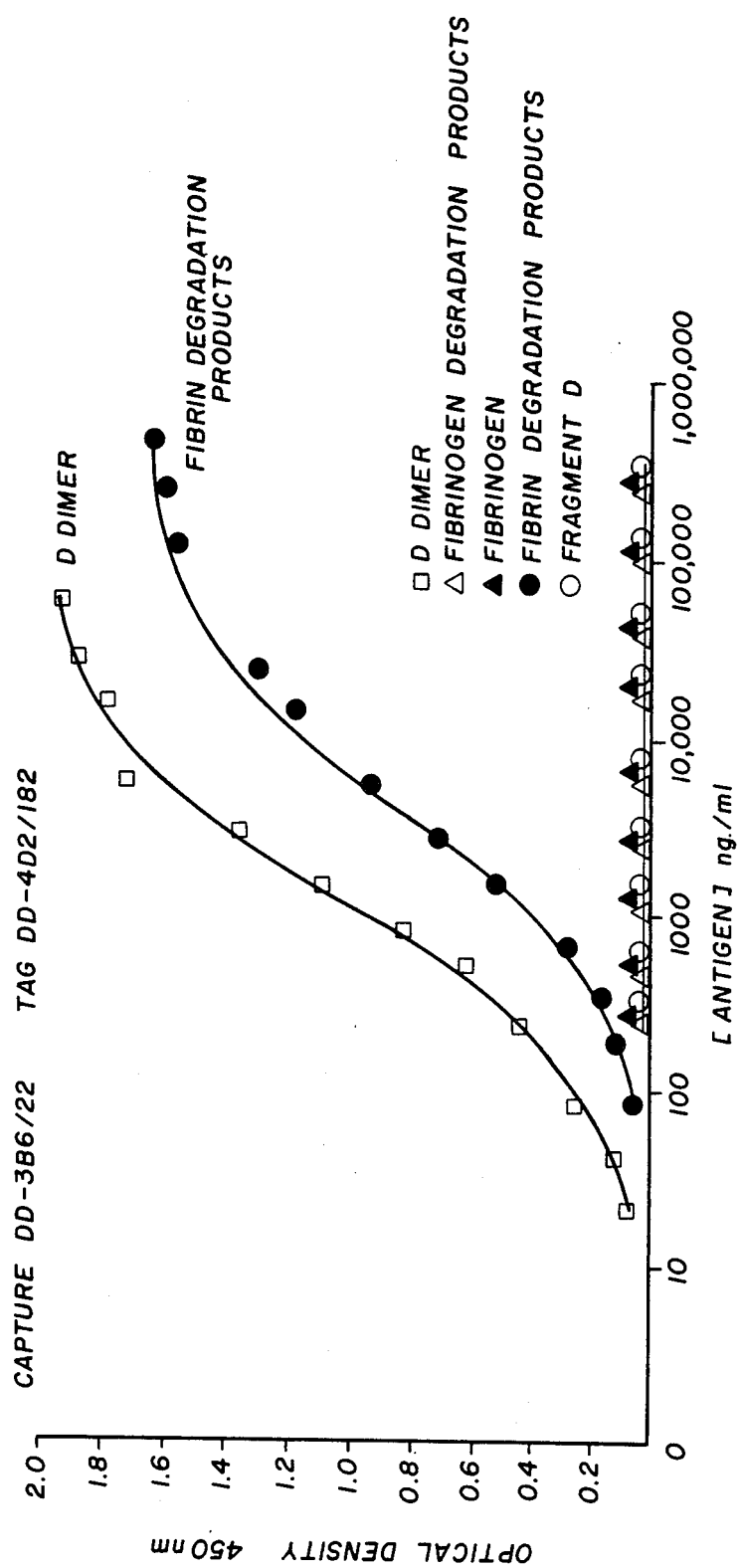

The above methods of obtaining the crude antigenic fraction are in vitro methods. A suitable in vivo method would be to obtain sera or other body fluid containing the crosslinked fibrin derivative from an animal including humans and subject the body fluid to a PAGE process wherein substantially pure crosslinked fibrin derivative may be isolated.

Alternatively crosslinked fibrin derivatives could be purified from serum obtained from patients suffering severe thrombotic disorders based on a technique using gel filtration in combination with ion exchange chrmoatography as described in Willner et al in *Biochemistry*, Vol. 21 pp 2687–2692 (1982) where human fibrinogen, purified fragments D, E and D dimer were prepared.

When using a pure crosslinked fibrin derivative such as D dimer, care must be taken in its preparation to not denature the molecule as it is susceptible to denaturation fairly easily.

For a more complete description of the abovementioned methods in preparing an antigenic extract which is usually of a crude nature reference may be made to the abovementioned Graeff and Hafter article. Suitable crosslinked fibrin derivatives for use in the invention may be any one of those previously described but preferably the derivative is $D_2E$ or D dimer and most suitably the derivative for use in the invention is D dimer.

In step (ii) a suitable animal to which the derivative or extract thereof may be administered is a mouse or rat. A mouse is preferred. It is also preferred to administer crude extract one or more times initially and follow this up with administration of pure or substantially pure crosslinked fibrin derivative. This procedure is preferred so that the task of obtaining monoclonal antibodies specific to the derivative is simplified.

After administration the mice which have had derivative or extract administered thereto are suitably killed and the spleens removed for subsequent processing to form a cell suspension. Further purification of the cell suspension may take place (e.g. by centrifugation) to isolate spleen white blooc cells or lymphocytes which may be fused with mouse myeloma cells.

The cloning technique may be broadly based on the technique described in Galfre et al in *Nature*, Vol. 266, pp. 550-2 (1977) where polyethylene glycol is used as the cell fusing agent to form a hybridoma cell which may then be cloned or recloned as desired suitably or the basis of limiting dilution using appropriate cell feeder layers.

Preferably for the cultivation of hybridoma cells well plates are utilized wherein cell suspensions are placed in each well with appropriate cell cultivation media.

It is preferred to remove samples of cells for screening assays and these may be carried out as described hereinafter. A number of the strongest growth wells are suitably chosen for maintenance on the basis of the screening assays. After the screening assays it is possible to chose a number of specific anitbody producing clonotypes to produce monoclonal antibody secreting cell lines by limiting dilution.

On the basis of further screening assays carried out on samples taken from well plates incorporating the limiting dilution clonotypes a number of specific antibody produced clones may be chosen for expansion to mass culture.

A suitable screening assay for use in the abovementioned process may comprise the steps of:
(a) coating a surface with an antigen selected from crosslinked fibrin derivative or extract containing same or fibrinogen degradation product,
(b) contacting the antigen in step (a) with a monoclonal antibody derived from fibrin crosslinked derivative prepared as described above,
(c) subjecting the complex formed in step (b) to a signal amplification step.

Suitably in step (a) a well plate may be utilized in which crosslinked fibrin derivative such as D dimer and/or fibrinogen degradation product (preferably obtained from a procedure wherein fibrinogen was suitably digested with thrombin to obtain fragment D, fragment E and optionally fragments X and Y) was applied to the individual wells.

Subsequently, a monoclonal antibody derived from a crosslinked fibrin derivative was then added to each well. An appropriate signal amplification step which may be applied is an EIA step wherein an appropriate enzyme conjugate may be coupled to the complex and substrate subsequently added. Alternatively RIA, FIA, agglutination, adherance or chemi luminescence may be used as appropriate signal amplification steps.

The purpose of the screening assay procedure referred to above is to ensure that the cells being tested are producing an antibody specific to the relevant crosslinked fibrin derivative. There should be no reaction with fibrinogen or fibrinogen degradation products and a positive reaction with the derivative.

The invention also includes within its scope an assay procedure for the detection of the presence of a cross linked fibrin derivative including the steps of:
(1) contacting a monoclonal antibody prepared from a crosslinked fibrin derivative with a fluid sample suspected of containing an antigen derived from a crosslinked fibrin derivative or comprising a crosslinked fibrin derivative per se; and
(2) subjecting the complex formed step (1) to a signal amplification step.

In the abovementioned assay the crosslinked fibrin derivative is suitably D dimer, $D_2E$ or any other derivative of a high molecular weight nature as described above. The monoclonal antibody is prepared as decribed previously which is relevant to the particular crosslinked fibrin derivative being assayed.

The single amplification step may be any one of those already described in relation to the screening assay procedure but is suitably EIA.

The presence of the crosslinked fibrin derivative may be used as a suitable diagnostic aid for prethrombotic, thrombotic or other conditions that involve the formation and lysis of fibrin.

The assay of the invention may also be used for monitoring lytic therapy such as streptokinese therapy and tissue plasminogen activator therapy (TPA). An example of a prethrombotic state is a stress condition. Examples of thrombotic states include DIC, pulmonary embolus, thrombosis, invasive tumors and other thrombotic states described hereinafter.

The fluid sample may be obtained from any suitable body fluid such as lymph, serum, plasma or exudate.

The assay procedure may be performed using a tube, well plate or micro plate as described previously or may be carried out in any other suitable manner including conventional procedures. A "stick" procedure using a single elongate member may be utilized wherein Ag or Ab is initially coated thereon before application of steps (b) and (c).

In another embodiment of the invention the monoclonal antibodies can be covalently attached to small beads. Such beads enable a quick (e.g. 2–3 minute) test to be carried out in serum plasma or other body fluids for the presence of crosslinked fibrin derivatives. The beads may be formed from polystyrene, nylon, glass or other suitable material. In relation to polystyrene, the MAb can be coupled thereto using the carbodiimide method as described in Molday et. al in *J. Cell Bio*, Vol. 64, page 75 (1975). For nylon beads a suitable coupling procedure is described in Hendry and Herrman J. in *Immun. Method*, Vol. 35, page 285 (1980) using glutaraldehyde. For glass beads a suitable coupling procedure using silaning agents may be utilized as described in U.S. Pat. No. 4,210,723. In these beads assays or latex assays when the beads which have already been coupled to MAbs are tested with test serum or plasma or other body fluid they may be checked for agglutination by use of a suitable calibration standard. In this embodiment latex particles or beads are prepared as uniform spheres of known refractive index and used as calibration standards for light scattering magnification, shadow angle, thickness of shadow material, scanning and transmission electron microscopy or laser scattering.

It will of course be appreciated that assays based on capture-tag techniques wherein a first MAb is captured by an antigen which is subsequentially tagged by a labelled second MAb (where the label may be suitably used in an EIA or RIA test)may be used in relation to this invention.

However, in some cases assays based on use of a single MAb may be used such as the abovementioned bead or latex assays described above.

In relation to an assay for a specific crosslinked fibrin derivative it has been found that of all the MAbs tested a number were discovered to be panspecific (i.e. binding to epitopes or reactive sites on fibrin breakdown products as well as fibrogen breakdown products) and others were monospecific (i.e. binding only to reactive sites on D dimer and other crosslinked fibrin derivatives).

When capture-tag experiments were carried out as discussed hereinafter in one type of assay a monospecific MAb was bound to a support surface and was tested with serum or other body fluid suspected of containing crosslinked fibrin derivative. When tagged with a second antibody which was a panspecific MAb attached to an appropriate label used in the signal amplification step this provided a precise assay for crosslinked fibrin derivative if the panspecific MAb bound to an epitope in the sample.

In a variation of this technique a panspecific MAb could be bound to a support surface and tested with body fluid suspected of containing the crosslinked fibrin derivative. Subsequently a monospecific MAb could be tagged to the body fluid antigen having a suitable label attached thereto.

In another version it is also possible to bind a first monospecific MAb to a support surface and test same with a sample of body fluid suspected of containing a crosslinked fibrin derivative. Subsequently a second monospecific MAb could be tagged to the body fluid antigen having a suitable label attached thereto.

In the following experiments human fibrinogen and purified fragments D, E and D dimer were prepared as described above in the Wilner reference. Fibrinogen degradation products were prepared as described in *Thromb Res*, Vol. 10, pp. 803–812, (1977), by Haverkate and Timan. Crosslinked fibrin which was necessary for the preparation of D dimer was prepared and digested with plasmin as described by Olexa and Budzynski *Biochemistry*, Vol. 18, page 991 (1979).

EXAMPLES

Cell Fusion and Selection of Hybrids

Spleens were removed aseptically from 2 immunized mice killed by cervical dislocation three days after an injection of D dimer. Previously the mice had been immunized with three injections of fibrin lysate digested with proteolytic enzymes thrombin and plasmin as reported in the aforementioned Graeff and Hafter reference. Two spleens were placed in a 60 mm Petri dish (Falcon, 3001, Oxnard, Calif.) containing 5 ml complete medium (85% RPMI 1640, 15% fetal calf serum, 100 I.U./ml penicillin, 100 $\mu$/ml streptomycin and $2\times10^{-3}$M·Glutamine; Gibco, Grand Island, N.Y.). A cell suspension was prepared by decapsulating the spleen with $2\times18$ gauge needles attached to 3 ml disposable syringes with the last cm of the tip bent through an angle of 60°. The cell suspension was then aspirated into a 10 ml syringe fitted with a 22 gauge needle and ejected with moderate pressure. This operation was performed twice before filtering the cells into a Falcon 2001 tube through a fine mesh stainless steel screen to remove larger cell clumps and debris.

The cell suspension was allowed to stand for 5 minutes at room temperature to allow smaller clumps and membrane fragments to settle before transferring the cell suspension to a fresh Falcon 2001 tube. The cells were centrifuged at 350G for 5 minutes at room temperature and the supernatant was decanted from the first cell pellet to a fresh tube and spun at 700G for five minutes to give a second cell pellet and the two pellets were pooled and resuspended in 5 ml complete medium. The spleen white blood cells (SWBC) were then counted and their viability estimated by Turks and Trypan blue stains respectively, and $100\times10^6$ viable SWBC were placed in separate Falcon 2001 tubes in a total volume of 5 ml complete medium. The NS-1 myeloma cells to be used for fusion, were washed once by centrifugation at 380G for 15 minutes at room temperature and adjusted to $5\times10^6$ viable cells/ml in complete medium.

Twenty-five$\times10^6$ NS-1 and $100\times10^6$ immune SWBC were mixed and spun at 350G for 5 minutes at room temperature. The supernatant was decanted, the remaining medium was carefully removed with a Pasteur pipette and 2 ml of a 42% (w/v) solution of polyethylene glycol (PEG, MW1540) (Baker Chemical Co., New Jersey) In RPMI 1640 containing 15% (v/v) dimethyl sulfoxide (DMSO) at 37° C. was added with a 5 ml glass disposable pipette (Corning Glass, Corning, N.Y.) and the cells were resuspended with the same 5 ml pipette for 30 seconds with the aid of an electric pipetter (Pipet-aid Drumond Scientific Co., Broomall, Pa.). The PEG-cell suspension was allowed to stand for a further 30 seconds at room temperature before adding 5 ml complete medium, dropwise, with a Pasteur pipette, over a period of 90 seconds with constant flicking of the tube, sufficient to ensure complete mixing with the viscous PEG solution. A further 5 ml complete medium was immediately added and mixed by inversion and the cell suspension was allowed to stand for a further 150 seconds at room temperature before centrifugation at 350G for 5 minutes at room temperature. The supernatant was decanted and the cell pellet was gently resuspended in 5 ml complete medium using a 5 ml pipette with the electric pipetter; extreme care was taken not to break up all cell clumps. Using a Tridak stepper (Bellco Glass Inc., Vineland, N.J.), 0.05 ml of the cell suspension was added to each well of 4 Costar 24 well plates (Costar 3524, Cambridge, Mass.) containing $1 \times 10^6$ normal BALB/c mouse SWBC as feeder cells in 1 ml complete medium containing $10^{-4}M$ Hypoxanthine (Sigma), $4 \times 10^{-7}M$ Aminopterin (Sigma), $1.6 \times 10^{-5}M$ Thymidine (Sigma) and $4 \times 10^{-5}M$ 2-Mercaptoethanol (HAT medium), hereafter referred to as 1° fusion plates.

The 1° fusion plates were then placed in a humidified 5% $CO_2$ 95% air atmosphere at 37° C. The cells were first fed either on days 5 or 7 and thereafter when necessary, with 0.5 ml fresh HAT medium. Generally, on day 10, 0.5 ml of the medium was removed for the screening assay from each well showing hybridoma growth and 0.5 ml fresh HAT medium was replaced. A number of the strongest growth wells were chosen for maintenance on the basis of the screening assay. The chosen wells were allowed to grow to confluency in the original well (1° well), then each was plit in half and transferred to a fresh well (2° well) of a 24 well Costar plate (2° plate). The wells were checked daily and expanded to a 2nd, 3rd or 4th well of the 2° 24-well Costar plate when necessary. From days 14–28, cells were fed with HT medium. When there was strong growth in at least 2 wells of the 2° plate, supernatant from one well of each clonotype was chosen for rescreening and a number of specific antibody producing clonotypes were chosen from the results of the second screening assay to produce monoclonal antibody secreting cell lines by limiting dilution.

Cloning of Hybridomas

One 2° well of each chosen clonotype was resuspended and the number of viable cells per well was estimated by Trypan blue exclusion. Immediately before plating each clonotype, the relevant series of dilutions were made in HT medium or complete medium (if the cells were older than 28 days post fusion) to give a frequency of 0.5 cells/0.05 ml. This volume was then added with a Tridak stepper to each well of a 96 well flat bottomed tissue culture plate (Flow Laboratories, Mississauga, Ontario, Canada) (L D plate) containing $1 \times 10^5$ normal mouse spleen feeder cells in 0.1 ml HT or complete medium. The LD plates were then placed in a 37° C. humidified 5% $CO_2$, 95% air atmosphere and screened for clonal growth 7–10 days later. From each positive growth well, 0.1 ml supernatant was removed for screening and these wells were fed for the first time with 0.1–0.15 ml HT or complete medium. On the basis of the LD screening assay, a minimum of 2 of the 'better' specific antibody-producing clones were finally selected for expansion to mass culture.

Alternatively if it was desired to obtain a large amount of MAb, female BALM/c mice were given an intraperitoneal injection of 0.5 ml 2, 5, 10, 14, tetramethylpentadecane (Pristane, Aldrich Chemical Corp., Milwaukee, Wis.) 14 days prior to the injection of $2 \times 10^6$ viable hybridoma cells and ascites fluids were collected from the mice 12 to 14 days after injection of the cells. The ascitic fluid was clarified by centrifugation and MAb were recovered by precipitation with 45% ammonium sulphate and stored at either 4° C. or −70° C. in phosphate buffered saline (PBS) containing 0.01% sodium azide.

Monoclonal antibody screening assay

The wells of a 96 well U bottomed microtest plate (Disposable Products Pty. Ltd., Adelaide, South Australia) were coated by adding 50 µl of either D dimer (5 µg/ml) or Fibrinogen degradation products (5 µg/ml in PBS for one hour at room temperature (25° C.). Excess antigen was removed by inverting and tapping the plate and the plate was then washed three times with PBS containing 0.05% Tween 20 (Sigma Chemical Corp., St. Louis, Mo.). Clones secreting MAb to D dimer or Fibrinogen degradation products were then detected by adding 50 µl of tissue culture supernatant to each well and incubating for one hour at room temperature. Unbound MAB was removed by inversion and tapping and the plate was washed three times with PBS/Tween. One hundred µl of a 1/1000 dilution of peroxidase conjugated rabbit antimouse immunoglobulin (Dakopatts, Copenhagen, Denmark) in PBS/Tween was added and allowed to incubate a further one hour at room temperature. The plate was again inverted and washed three times with PBS/Tween and 100 µl of activated substrate (immediately before use 10 µl of a 3% solution of hydrogen peroxide was added to 10 ml of a substrate solution containing 50 mM citrate, 2.5 mM of o-tolidine dihydrochloride (o-tolidine, Sigma Chemical Co. recrystallized from dilute HCl) 0.025 mM EDTA pH 4.5)was added to each well. The color reaction was stopped after 10 minutes by the addition of 50 µl of 3M HCl which caused a color change from blue to yellow and the absorbance was recorded at 450 ηm on a Titertek multiscan.

Peroxidase conjugation

Conjugation of the D dimer monoclonal antibodies was carried out by a modification of the method of Nakane and Kaiwoi, *J. of Histochem and Cytochem,* Vol. 22, pp. 1084-91, (1974) with peridoate oxidized peroxidase. 5 mg/ml peroxidase in distilled water was mixed with a 1/5 volume of 0.1M sodium periodate for 20 minutes at room temperature and unreacted periodate was removed by gel filtration on a column of Sephadex G25 equilibrated with 0.001M citrate pH 4.5. Monoclonal antibody (in PBS) was added in a ratio of 2 mg antibody per mg peroxidase and the pH was immediately adjusted to pH 9.0–9.5 by the addition of 1M sodium carbonate, pH 9.5. The reaction was allowed to proceed for 2–3 hours at room temperature with occasional mixing and stopped by the addition of 1/10th volume 2.0M ethoanolamine pH 9.5 Barbour, H. M., in *J of Immunol Meth.,* Vol. 11, pp 15–23, (1976). After sitting overnight at 4° C., ethanolamine was removed by gel filtration on a Sephandex G25 column equilibrated with PBS and the enzyme conjugate was stored at 4° C. in the presence of 0.01% methiolate.

Protein Determination

Protein determination was carried out by the method of Rylatt and Parish, in *Analytical Biochem*, Vol. 121 pp. 213-214 (1982). *Capture/Tag Experiments and D dimer assay*

Antigen capture/tag experiments were performed by incubating each well of a 96 well microtitre plate with 50 μl (10 μg/ml) of each of the relevant MAb in PBS for 1 hour at room temperature. Unbound MAb was removed by inversion and tapping the plate followed by washing with PBS/Tween as described for the screening assay. Antigen capture was then achieved by adding 50 μl of each antigen (0-1 mg/ml) in PBS/Tween to the MAb coated wells for 1 hour at room temperature. The wells were washed as previously described. Captured antigen was then tagged with peroxidase conjugated MAb by adding 50 μl (1 μg/ml) of the various peroxidase conjugated MAb in PBS/Tween to each well for one hour at room temperature. After washing, the presence of bound conjugate was determined by the addition of 100 μl substrate as described in the screening assay. For the determination of the presence of crosslinked derivatives in plasma or serum, 50 μl of a 1/5 dilution of plasma or serum in PBS/Tween was incubated instead of antigen at the second step.

RESULTS

Specificity

Several hundred hybridoma clones secreting MAb against human D dimer were initially identified by enzyme immunoassay and two different classes of MAb were obtained (TABLE 1). The first group which contained the vast majority of positive clones (examples of which were B44.7.4D2/182 (DD-4D2/182), B44.7.2C1/19 (DD-2C1/19), B41.7.2D5/38 (DD-2D5/38), produced MAb that bound to epitopes present on intact fibrinogen, an extract containing fibrinogen degradation products, fragment D and D dimer. However, the abovementioned first group did not bind to fragment E. The second and much smaller group (examples of which were B42.7.3B6/22 (DD-3B6/22) and B41.7.1C3/108 (DD-1C3/108)), reacted with determinants present on D dimer but not on fragment D.

No cross reaction was found with purified intact fibrinogen or fibrinogen degradation products.

D dimer monoclonals as captured antibodies

In order to establish whether the various MAb were reacting with the same or distinct sites on D dimer, capture/tag experiments were carried out. The wells of a 96 well micro plate were coated with each MAb and incubated with either fibrinogen breakdown products or D dimer. After washing away unbound protein, peroxidase conjugated MAb were added and after washing the presence of bound conjugate was determined by the addition of activated substrate (TABLE 2).

DD-2C1/19

This MAb was able to combine with the monospecific MAb DD-IC3/108 or DD-3B6/22 only when D dimer was utilized as antigen and the panspecific MAb DD-2D5/38 when either fibrinogen as degradation products of D dimer antigens were used. It was unable to combine with the other panspecific MAb DD-4D2/182 with either antigen. These results suggest that DD-2C1/19 binds close to the site recognize by DD-4D2/⅔but to epitopes quite distinct to those recognized by DD-2D5/38, DD-IC3/108 or DD-3B6/22.

DD-4D2/182

The panspecific MAb DD-4D2/182 had a specificity pattern analogous to DD-2C1/19. The results suggest that DD-4D2/182 and DD-2C1/19 may have very close or overlapping binding sites.

DD-2D5/38

The panspecific MAb DD-2D5/38 was also able to combine with DD-1C3/108 and DD-3B5/22 only when D dimer was used but was capable of combining with both of the other panspecific MAb DD-4D2/182 and DD-2C1/19 with either D dimer or fibrinogen degradation products as antigens. This monoclonal was the only one of this series which was capable of combination with itself, suggesting the presence of at least two binding sites per D dimer molecule. However, it is clear that these binding sites must be distinct from the sites recognized by the other four monoclonals.

DD-3B6/22 and DD-1C3/108

The D dimer specific MAb DD-3B6/22 was capable of combining with any of the panspecific monoclonals DD-4D2/182, DD-2C1/19 or DD-2D5/38 when D dimer was the captured antigen. MAb DD-1C3/108 had a smaller specificity pattern, however it performed relatively poorly as the capture MAb. Overall the results suggest that this set of monoclonals binds to three distinct areas on the D dimer molecule, a unique site recognized by DD-2D5/38, another shared by DD-4D2/182 and DD-2C1/19 and a D dimer specific site shared by DD-1C3/108 and DD-3B6/22.

A specific assay for D dimer

Figure 2:
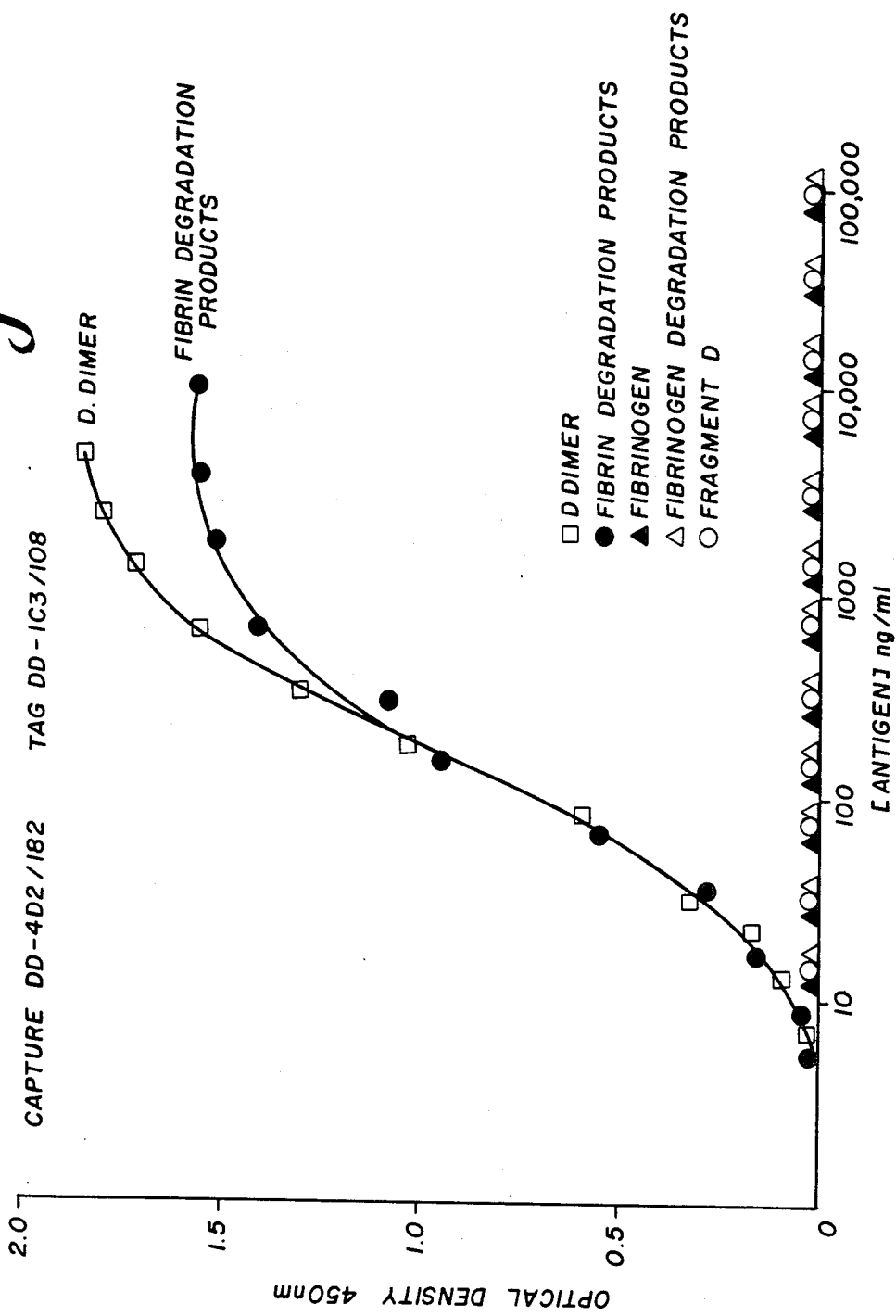

The results above suggested that several combinations of these MAb might prove useful in developing a specific assay for D dimer and perhaps lead to a general assay for fibrinolysis. In the first type of combination, the monospecific MAb DD-3B6/22 was used as a capture MAb and antigen was tagged with either of the panspecific MAb DD-4D2/182 or DD-2D5/38. An assay using peroxidase conjugated DD-4D2/182 as a tag MAb had a sensitivity of 10-20 ηg/ml of D dimer (FIG. 1). There was a strong reaction with fibrin degradation products but no reaction was seen with fibrinogen degradation products or fragment D. Essentially identical results were obtained using peroxidase conjugated DD-2D5/38 as the tag MAb (not shown). In another type of combination the panspecific monoclonal DD-4D2/182 was used as the capture MAb and the antigen was tagged with peroxidase conjugated DD-1C3/108 (FIG. 2). In this case 10-20 ηg/ml concentrations of both D dimer and fibrin degradation products produced clear signals but there was no detectable cross-reaction with either intact fibrinogen, fibrinogen degradation products or fragment D. Qualitatively similar results were obtained capturing with either DD-2C1/19 or DD-2D5/38 (not shown).

Assays based on both these monoclonal combinations were investigated for their ability to detect D dimer and other crosslinked derivatives in blood. Serum or plasma diluted 1/5 in PBS/Tween from either normal healthy volunteers (control was 19, 20, 23) or from patients with clinically diagnosed DIC were incubated with micro plates coated with either DD-3B6/22 or DD-4D2/82 and after incubation for one hour at room temperature the presence of bound D dimer or crosslinked derivative was established by addition of the relevant conjugated MAb (Table 3). Assays based on DD-3B6/22 gave positive results with both serum and plasma whereas those based on DD-1C3/108 gave positive results with serum only.

LATEX BEAD TEST

Latex particles are polystyrene beads approximately 1 micron in diameter to which has been covalently attached the monoclonal antibody DD-3B6/22.

TESTING PROCEDURE 1. 0.02 ml beads were mixed on a slide (shaken before use) with 0.01 ml of serum or diluted sample under test.
2. The slide was rocked gently for 2 minutes and the presence or absence of agglutination was noted.

ESTIMATION OF LEVEL OF CROSSLINKED FIBRIN DERIVATIVES

Figure 4:
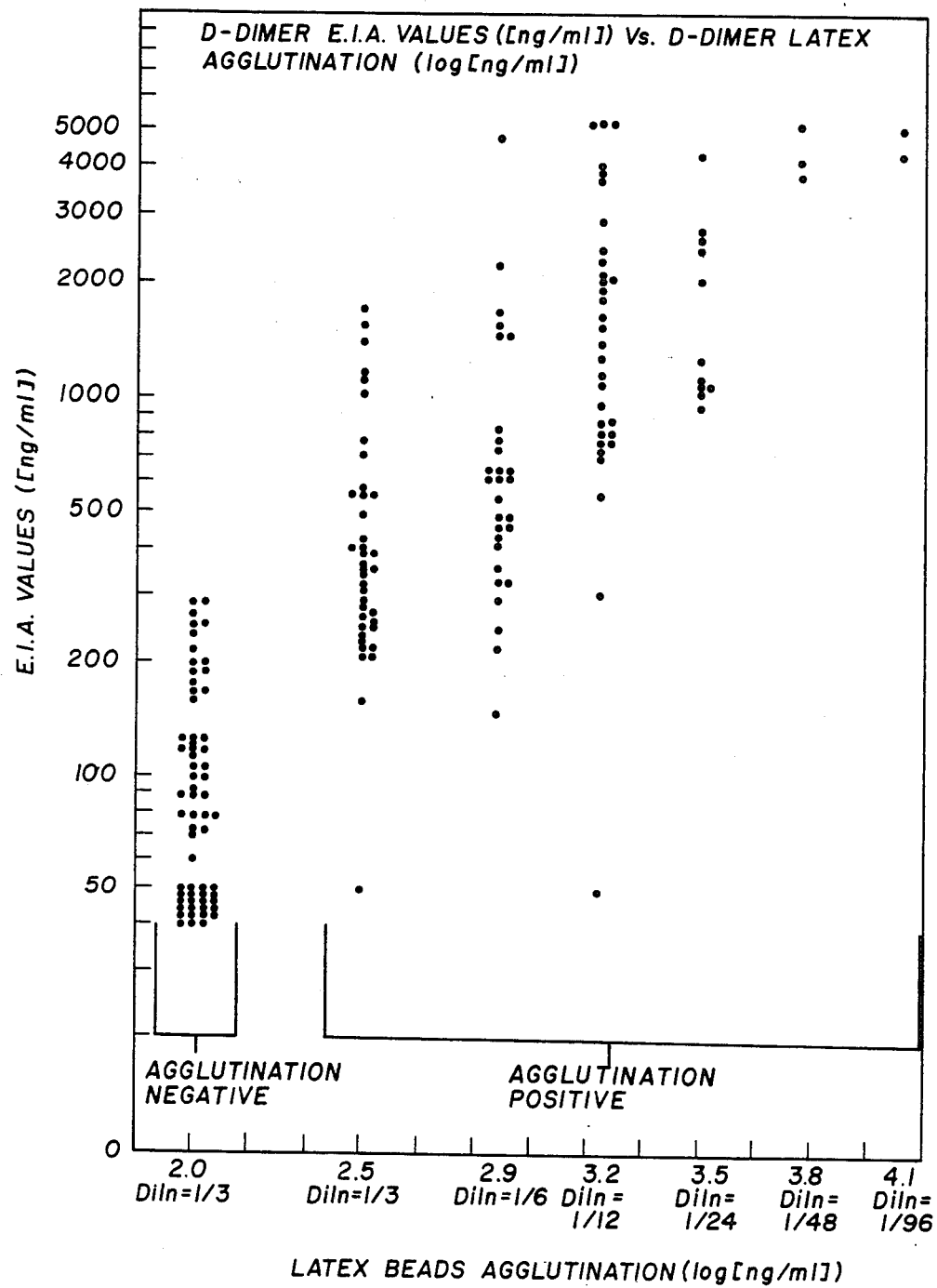
FIG. 4 shows latex bead tests or positive aggutination results.

Positive agglutination was obtained with samples containing >200 ηg/ml crosslinked derivative. More accurate estimates of higher levels of crosslinked derivatives in a particular sample were obtained by serial dilutions of the sample in PBS buffer as illustrated in FIG. 4.

FURTHER CLINICAL TRIALS

Subjects

Figure 3:
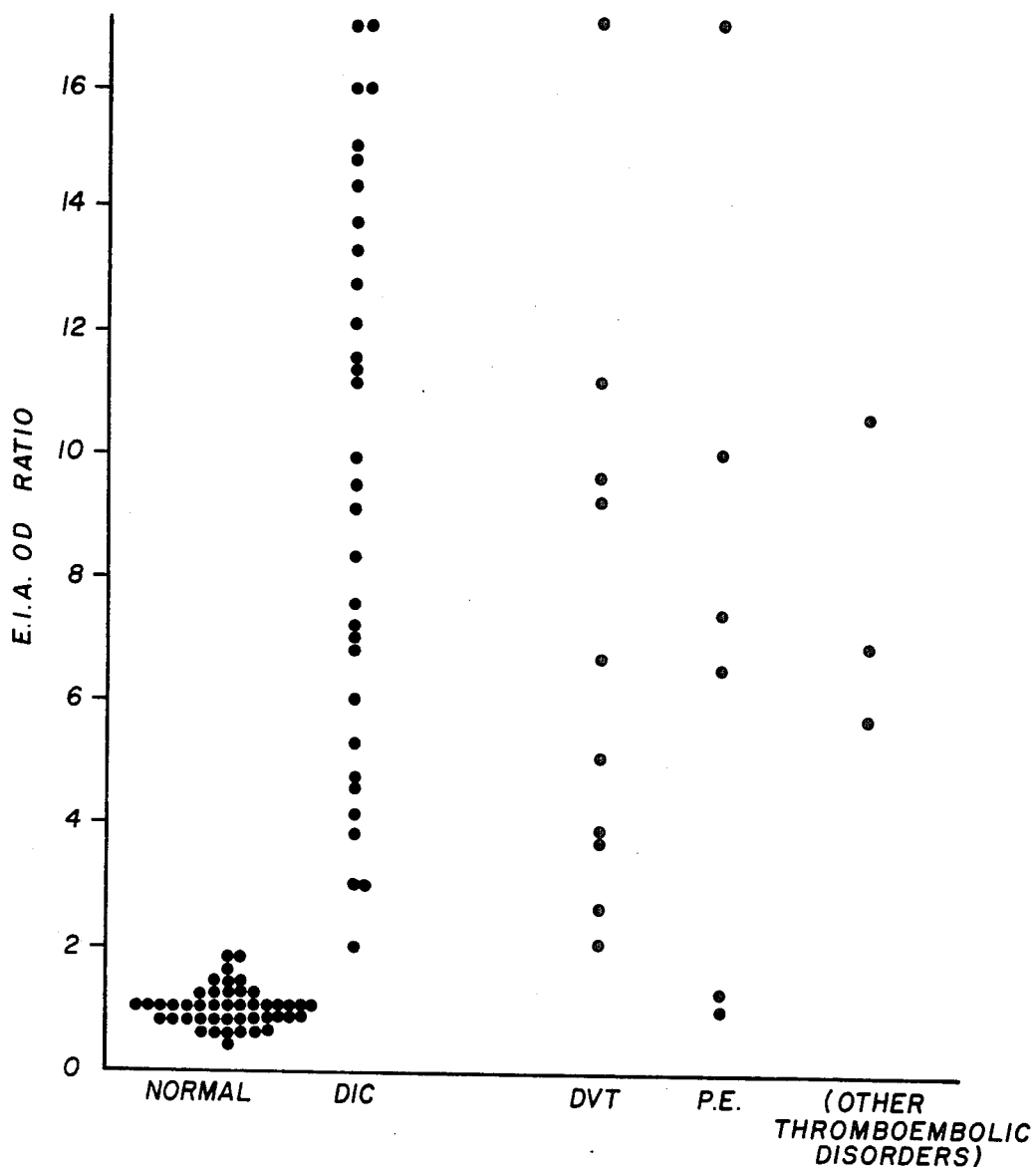
FIG. 3 is a graphical representation of the data shown in Tables 4, 5, 6, and 7. Thus normal healthy volunteers are shown in the left hand column, DIC patients in the second column from the left DVT patients in the third column and pulmonary embolus in the last column.

The groups studied were (a) 45 healthy laboratory volunteers as controls; (b) 10 patients with venographically proven deep venous thrombosis and/or arterial thrombosis; (c) 6 patients with pulmonary embolism and (d) 30 patients with laboratory evidence of consumption coagulopathy and diagnoses characteristically associated with disseminated intravascular coagulation. The patients in group (d) all fulfilled the criteria for disseminated intravascular coagulation as described in Whaun and Oski in *Can. Med. Assc. J.* Vol. 107 pp. 963–66 (1972). Two ml of blood was clotted with thrombin (20 iu) in the presence of soy bean trypsin inhibitor (Becton and Dickinson 3.67 n.f. units) and the serum was used to assay soluble crosslinked fibrin derivatives using the capture/tag method previously described. Results in terms of $D_2$ ratio (ratio of sample compared to blank) are given in Table 4 for group (a), Table 5 for group (d), Table 6 for group (b) and Table 7 for group (c). The results are also plotted graphically in FIG. 3.

Previous attempts to obtain specific antibody probes to discriminate crosslinked fibrin derivatives have been hampered by the nature of the polyclonal antibody response to the antigens used for immunzation. Several antibody preparations have already been described with a marked preference for the crosslinked derivative—50 fold greater reactivity for D dimer compared to D (see the aforementioned Budzynski reference) or 100 fold for crosslinked γ—γchains compared to non-crosslinked and peptide (Purves et al, in *Biochemistry*, Vol. 19, pp. 4051-58 1980) or 8 fold for D dimer compared to fibrinogen or fibrinogen degradation products (Lahiri et al, in *Thromb Res,* Vol. 23, pp. 103–112 1981). The degree of cross-reaction with non-crosslinked fragments has been still enough to preclude their value as diagnostic reagents.

The problem of producing diagnostic reagents could not be overcome until monospecific MAb were produced (DD-3B6/22 and DD-1C3/108) that reacted only with crosslinked fibrin derivatives. These MAb have been employed to produce diagnostic assays of which capture/tag type systems are preferred. However conventional binding inhibition assays employing labelled monospecific DD-3B6/22, DD-1C3/108 or labelled crosslinked fibrin derivative could also be used.

In a capture/tag assay, the antigen in question is reacted with two antibodies with specificity for different regions of the same molecule. Usually a capture antibody is attached onto a solid phase and after addition of antigen to allow binding to occur, the presence of bound antigen can be detected after washing by the addition of the second labelled antibody.

MAb DD-1C3/108 although quite specifid for D dimer performed quite poorly as a capture MAb, yet the peroxidase conjugated MAb was a good tag. On the other hand, the other specific monoclonal DD-3B6/22 was a good capture MAb but a relatively poor tag.

Assays based on DD-1C3/108 as a tag bound D dimer and fibrin breakdown products equally, whereas assays using DD-3B6/22 as a capture MAb bound D dimer approximately 100 fold better. Similarly a signal can be generated with high concentrations of fibrinogen with the DD-3B6/22 assay but not DD-1C3/108. Each of these monoclonals shows a similar degree of cross-reaction with both these antigens in the standard enzyme immunoassay (Table 1).

Both of these assays can detect low levels of D dimer or other crosslinked derivatives present in serum from patients with DIC but is is not surprising that the high levels of fibrinogen present in plasma (approx, 3000 μg/ml) would prevent assays based on MAb DD-1C3/108 as a tagging antibody from giving positive results with plasma. The capture antibody in this case DD-4D2/182 has a strong reaction with both fibrinogen and D dimer and the relatively high concentration of fibrinogen in plasma might be expected to swamp the capture monoclonal on the solid phase. On the other hand the plasma assay based on the monospecific DD-3B6/>will selectively capture crosslinked derivatives even in the presence of several orders of magnitude higher concentrations of fibrinogen (FIG. 2) and is therefore more efficient in relation to assay of crosslinked fibrin derivatives.

The latex bead assay results as shown in FIG. 4 correlated with the other experimental results obtained in EIA referred to previously. The latex bead assay therefore offers rapid diagnostic test potential.

The abovementioned assay procedures may be carried out between 4°–40° C. but more suitably at room temperature. The contact between the test sample and the relevant MAb may be carried out at a pH of 5–9 with a suitable upper limit of ionic strength being IM.

TABLE 1

Specificity of D dimer monoclonal antibodies: cross reaction with fibrinogen and fibrinogen degradation products

| Monoclonal | Fibrinogen | Antigen Fibrinogen Degradation Products | Fibrin Degradation Products | D | E | D Dimer | Titre |
|---|---|---|---|---|---|---|---|
| DD-4D2/182 | 255 | 71 | 35 | 23 | 0 | 100[1] | $\frac{1}{2.5 \times 10^6}$ [2] |
| DD-2C1/19 | 156 | 68 | 35 | 28 | 0 | 100 | $\frac{1}{2.5 \times 10^6}$ |
| DD-2D5/38 | 423 | 111 | 80 | 37 | 0 | 100 | $\frac{1}{2.5 \times 10^6}$ |
| DD-3B6/22 | 4 | 3 | 45 | 0 | 0 | 100 | $\frac{1}{2.5 \times 10^6}$ |
| DD-1C3/108 | 2 | 0 | 31 | 0 | 0 | 100 | $\frac{1}{2.5 \times 10^5}$ |

[1] Optical density for the reaction against D dimer for each monoclonal was taken to be 100%. The values then represent cross-reactions as determined by the relative optical density obtained with the other antigens.
[2] The titre is the lowest dilution which gives a reading using D dimer as the antigen of $A_{450nm} > 0.1$.

TABLE 2

Antigen capture with D dimer monoclonal antibodies

| | Antigen | | | | | | | | | |
|---|---|---|---|---|---|---|---|---|---|---|
| | | Fibrinogen Degradation Products | | | | | D dimer | | | |
| Capture MAb | Tag DD-2C1/19 | DD-4D2/182 | DD-2D5/38 | DD-3B6/22 | DD-1C3/108 | Tag DD-2C1/19 | DD-4D2/182 | DD-2D5/38 | DD-3B6/22 | DD-1C3/108 |
| DD-2C1/19 | 0 | 0 | 0.36 | 0 | 0 | 0 | 0 | 0.43 | 0.21 | 0.30 |
| DD-4D2/182 | 0 | 0 | 0.29 | 0 | 0 | 0 | 0 | 0.31 | 0.24 | 1.80 |
| DD-2D5/38 | 0.41 | 0.51 | 0.11 | 0 | 0 | 0.34 | 0.35 | 0.11 | 0.16 | 0.90 |
| DD-3B6/22 | 0 | 0 | 0 | 0 | 0 | 0.20 | 1.63 | 1.04 | 0 | 0 |
| DD-1C3/108 | 0 | 0 | 0 | 0 | 0 | 0 | 0.07 | 0.11 | 0 | 0 |

The values are expressed as a change in $A_{450nm}$ obtained after a 10 minute incubation with substrate compared to a control experiment in which PBS/T was incubated with the capturing monoclonal instead of the relevant antigen.

TABLE 3

The determination of the presence of crosslinked fibrin derivatives in blood by enzyme immunoassay

| Sample | DIC Score[1] | DD-3B6/22 Capture Serum | Plasma | DD-1C3/108 Tag Serum | Plasma | D dimer Gel |
|---|---|---|---|---|---|---|
| MS 8 | 8 | 0.223[2] | 0.627 | 0.452 | 0.007 | +[3] |
| MS 9 | 7 | 0.704 | 1.153 | 0.584 | 0.013 | + |
| MS 11 | 9½ | 0.323 | 0.393 | 0.587 | 0.004 | + |
| MS 14 | 9 | 0.272 | 0.296 | 0.227 | 0.000 | + |
| NFC 19 | — | 0.000 | 0.047 | 0.051 | 0.013 | — |
| 20 | — | 0.007 | 0.037 | 0.081 | 0.013 | — |
| 23 | — | 0.014 | 0.040 | 0.092 | 0.013 | — |

[1] DIC Score The patients were diagnosed as having Disseminated Intravascular Coagulation according to the scoring system of Whaun and Oski, Can. Med. Assoc. J. 107, 963–66 (1972)
[2] The values are expressed as change in $A_{450nm}$ relative to a control experiment in which PBS/Tween was incubated with capturing MAb instead of the relevant antigen.
[3] The presence of D dimer by polyacrylamide gel electrophoresis was established according to the method of Lane D.A. et al, Thromb. Res., 9, 191–200 (1976).

TABLE 4

Normal healthy Volunteers

| No. | $D_2$ Ratio[1] | No. | $D_2$ Ratio[1] |
|---|---|---|---|
| 1 | 0.7 | 24 | 1.2 |
| 2 | 0.7 | 25 | 1.5 |
| 3 | 0.7 | 26 | 1.2 |
| 4 | 1.2 | 27 | 0.8 |
| 5 | 1.1 | 28 | 1.1 |
| 6 | 0.9 | 29 | 0.3 |
| 7 | 0.7 | 30 | 0.7 |
| 8 | 0.6 | 31 | 0.7 |
| 9 | 0.5 | 32 | 1.0 |
| 10 | 0.5 | 33 | 1.0 |
| 11 | 1.2 | 34 | 1.0 |
| 12 | 1.2 | 35 | 1.0 |
| 13 | 0.8 | 36 | 1.0 |
| 14 | 0.6 | 37 | 1.0 |
| 15 | 0.9 | 38 | 1.0 |
| 16 | 0.5 | 39 | 1.0 |
| 17 | 0.6 | 40 | 1.0 |
| 18 | 0.7 | 41 | 1.5 |
| 19 | 0.8 | 42 | 0.5 |
| 20 | 0.6 | 43 | 0.5 |
| 21 | 0.7 | 44 | 1.0 |
| 22 | 0.4 | 45 | 1.0 |
| 23 | 1.0 | | |

[1] $D_2$ Ratio derived from $\frac{A_{450} \text{ test sample}}{A_{450} \text{ control}}$ n = 45
x̄ = 0.9
SD = 0.3

TABLE 5

Disseminated Intravascular Coagulation Patients

| No. | Clinical Condition | DIC Score[1] | $D_2$ Ratio[2] | Page Analysis[3] |
|---|---|---|---|---|
| 1 | Disseminated Breast Carcinoma, Pulmonary Embolus and Bleeding | 8 | 13.3 | + |
| 2 | Lacerated Placenta and Post Partum | 7 | 14.8 | + |

TABLE 5-continued

Disseminated Intravascular Coagulation Patients

| No. | Clinical Condition | DIC Score[1] | $D_2$ Ratio[2] | Page Analysis[3] |
|---|---|---|---|---|
| 3 | Disseminated Carcinoma, Venous Thrombosis and post Surgery Bleeding Hemorrhage | 7½ | 15.7 | + |
| 4 | Lymphoma, Ascites, Le Veen Shunt | 7 | 18.7 | + |
| 5 | Alcoholic Liver Disease, Septicemia and Bleeding | 8 | 12.2 | + |
| 6 | Hemorrhagic Pancreatitis and Septicemia | 7 | 14.7 | + |
| 7 | Acute Renal Failure, Septicemia, and Bleeding | 9½ | 9.2 | + |
| 8 | Bleeding Oesophageal Varices | 9 | 3.7 | + |
| 9 | Analgesic Nephropathy and Septicemia | 7½ | 20.3 | + |
| 10 | Severe Pre-eclamptic Toxemia and Hemophtusis | 7½ | 13.8 | + |
| 11 | Multiple Injuries and Oozing Blood | 8½ | 14.3 | + |
| 12 | Alcoholic Liver Disease, Cirrhosis, Bleeding, and Thrombosis | 9 | 4.8 | + |
| 13 | Chronic Renal Failure and Septicemia | 7½ | 12.7 | + |
| 14 | Hodgkins Disease and Bleeding | 10 | 11.2 | + |
| 15 | Meningococcol Septicemia and Petechiae | 9 | 16.0 | + |
| 16 | Melaena, Hematuria and Purpura | 7 | 11.6 | + |
| 17 | Carcinoma of the Prostate | 8 | 9.5 | + |
| 18 | Disseminated Carcinoma and Microangiopathic Haemolytic Anemia | 8 | 11.3 | + |
| 19 | Acute Pancreatitis and Disseminated Thrombosis | 10 | 4.4 | + |
| 20 | Acute Pancreatitis, Acidosis and Bleeding | 10 | 2.9 | + |
| 21 | Alcoholic Liver Disease | 7 | 7.2 | + |
| 22 | Septicemia, Acute Respiratory Disease Syndrome and Bleeding | 7½ | 7.5 | + |
| 23 | Subacute Bacterial Endocarditis | 8½ | 6.0 | + |
| 24 | Severe Pre-eclamptic Toxemia | 7 | 6.8 | + |
| 25 | Chronic Renal Failure and Liver Disease | 8 | 2.9 | + |
| 26 | Septicemia | 8 | 2.0 | + |
| 27 | Severe Pre-eclamptic Toxemia | 8 | 4.5 | + |
| 28 | Promyelocytic Leukemia (M3) | 7 | 7.0 | + |
| 29 | Acute Pancreatitis and Bleeding | 7½ | 10.0 | + |
| 30 | Perinatal Hypoxia | 9 | 8.4 | + |

[1] DIC diagnosed according to Whaun and Oski, Can.Med Assc.J. 107, 963–966 (1972)

[2] $D_2$ Ratio derived from $\frac{A_{450} \text{ test sample}}{A_{450} \text{ control}}$

[3] The presence of D dimer or high molecular weight Fibrin degradation products established according to Lane et al, Thrombosis Res.,9,191–200 (1976)

TABLE 6

Deep venous thrombosis or arterial thrombosis patients

| No. | Clinical Condition | $D_2$ Ratio[1] |
|---|---|---|
| 1 | Deep Venous Thrombosis and Pulmonary Embolus | 24.9 |
| 2 | Cerebral Artery Thrombosis (Mitral Stenosis) | 9.6 |
| 3 | Left Femoral Artery Thrombosis | 2.6 |
| 4 | Recurrent Deep Venous Thrombosis | 5.0 |
| 5 | Right Deep Venous Thrombosis | 9.2 |
| 6 | Left Deep Venous Thrombosis | 3.6 |
| 7 | Left Deep Venous Thrombosis | 2.0 |
| 8 | Right Deep Venous Thrombosis | 6.6 |
| 9 | Left Deep Venous Thrombosis | 3.7 |
| 10 | Severe Chronic Liver Disease, Probable Thrombosis in the Inferior Vena cava | 11.2 |

[1] $D_2$ Ratio derived from $\frac{A_{450} \text{ test sample}}{A_{450} \text{ control}}$

TABLE 7

Pulmonary Embolus Patients

| No. | Clinical Condition | $D_2$ Ratio[1] |
|---|---|---|
| 1 | Deep Venous Thrombosis and Pulmonary Embolus | 24.9 |
| 2 | Pulmonary Embolus (Post operative) | 6.4 |
| 3 | High Probability of Pulmonary Embolus by Lung Scan | 1.0 |
| 4 | Low Probability of Pulmonary Embolus by Lung Scan | 7.4 |
| 5 | Possible Pulmonary Embolus | 1.2 |
| 6 | Pulmonary Embolus and Le Veen Shunt | 9.9 |

[1] D Ratio derived from $\frac{A_{450} \text{ test sample}}{A_{450} \text{ control}}$

We claim:

1. A screening assay for determining whether cells are producing antibody specific to a cross-linked fibrin derivative including the steps of:
   (A) coating a surface with antigen selected from
   (i) cross-linked fibrin derivative;
   (ii) extract containing said derivative; or
   (iii) fibrinogen degradation product;

(B) contacting said antigen with monoclonal antibody reactive only with cross-linked fibrin derivative to form a complex; and (C) detecting said complex formed in step (B).

2. An assay as claimed in claim 1 wherein in step (A) a well plate is utilized in which antigen is added to each well prior to said monoclonal antibody.

3. An assay procedure for detection of the presence of a crosslinked fibrin derivative in a fluid including the steps of:
   (i) contacting monoclonal antibody reactive only with crosslinked fibrin derivative, with a fluid sample suspected of containing an antigen derived from a crosslinked fibrin derivative or a crosslinked fibrin derivative per se, to form a complex; and
   (ii) detecting said complex formed in step (i).

4. An assay procedure as claimed in claim 3 wherein the crosslinked fibrin derivative is D dimer.

5. An assay procedure as claimed in claim 3 wherein a first monoclonal antibody in step (i) is bound or captured to an antigen in said body fluid which is subsequently tagged in step (ii) by a labelled second monoclonal antibody.

6. An assay procedure as claimed in claim 5 wherein said first monoclonal antibody is monospecific and said second monoclonal antibody is pan specific.

7. An assay procedure as claimed in claim 5 wherein said first monoclonal antibody is monospecific and said second monoclonal antibody is monospecific.

8. An assay procedure as claimed in claim 5 wherein said first monoclonal antibody is pan specific and said second monoclonal antibody is monospecific.

9. An assay procedure as claimed in claim 5 wherein the second monoclonal antibody is labelled with an enzyme which is subsequently reacted with a substrate for said enzyme.

10. An assay procedure as claimed in claim 5 wherein the second monoclonal antibody is labelled with a radioactive species.

11. An assay procedure in claim 3 wherein the monoclonal antibody in step (i) is initially coupled to latex beads before being contacted with said fluid sample and subsequently being checked for agglutination in step (ii).

12. A method of detection of crosslinked fibrin derivative in a body fluid including the steps of:
   (i) immunizing an animal with a crosslinked fibrin derivative or extract containing same;
   (ii) removing a spleen from the animal;
   (iii) treating the spleen to form a cell suspension;
   (iv) purifying the cell suspension to isolate spleen white blood cells or lymphocytes.
   (v) forming hybridoma cells containing as one component said spleen white blood cells or lymphocytes;
   (iv) cloning or recloning said hybridoma cells using appropriate cell feeder layers;
   (vii) carrying out screening assays with antigen selected from crosslinked fibrin derivative or extract containing same or fibrinogen degradation product so as to isolate hybridoma cells which produce monoclonal antibody reactive only with crosslinked fibrin derivative;
   (viii) contacting a fluid sample suspected of containing crosslinked fibrin derivative or antigen derived therefrom with monoclonal antibody prepared from hybridoma cells isolated after step (vii) to form a complex, and detecting said complex formed in step (viii).

13. A method of diagnosis of disseminated intravascular coagulation (DIC) and other thrombotic states including the steps of:
   (i) isolating a monoclonal antibody reacting with crosslinked fibrin derivative but not fragment D, fragment E, fibrinogen or fibrinogen degradation products;
   (ii) contacting said monoclonal antibody with a fluid sample from a patient suspected of suffering from DIC or other thrombotic state; and,
   (iii) analyzing for presence of cross-linked fibrin derivative in said sample to determine if the cross-linked fibrin derivative reacted with said monoclonal antibody.

14. A method of diagnosis of disseminated intravascular coagulation (DIC) and other thrombotic states including the steps of:
   (i) isolating a monoclonal antibody reacting only with crosslinked fibrin derivative;
   (ii) contacting said monoclonal antibody with a fluid sample from a patient suspected of suffering from DIC or other thrombotic state; and,
   (iii) analyzing for presence of cross-linked fibrin derivative in said sample to determine if the cross-linked fibrin derivative reacted with said monoclonal antibody.

15. A method as in claim 13 wherein said crosslinked fibrin derivative is D-dimer.

* * * * *

UNITED STATES PATENT AND TRADEMARK OFFICE
CERTIFICATE OF CORRECTION

PATENT NO. : 4,758,524

DATED : July 19, 1988

INVENTOR(S) : BUNDESEN et al.

It is certified that error appears in the above-identified patent and that said Letters Patent is hereby corrected as shown below:

ON TITLE PAGE:

Replace item (73) "Assignee: Fielder Gillespie David Limited" with
--Assignee: Fielder Gillespie Davis Limited--.

Signed and Sealed this

Twenty-first Day of July, 1992

*Attest:*

DOUGLAS B. COMER

*Attesting Officer*   Acting Commissioner of Patents and Trademarks